US00RE40432E

(19) United States
(12) Reissued Patent
Cavanagh

(10) Patent Number: US RE40,432 E
(45) Date of Reissued Patent: Jul. 15, 2008

(54) CONTAINER FOR SHARP INSTRUMENTS

(75) Inventor: Michael Shane Cavanagh, Bowen Mountain (AU)

(73) Assignee: Catilina Nominees Pty. Ltd., Victoria (AU)

(21) Appl. No.: 10/613,144
(22) PCT Filed: Apr. 29, 1997
(86) PCT No.: PCT/AU97/00259

§ 371 (c)(1),
(2), (4) Date: Jul. 21, 1998

(87) PCT Pub. No.: WO97/40753

PCT Pub. Date: Nov. 6, 1997

Related U.S. Patent Documents

Reissue of:
(64) Patent No.: 6,065,596
Issued: May 23, 2000
Appl. No.: 09/101,864
Filed: Jul. 21, 1998

(51) Int. Cl.
*B65D 85/24* (2006.01)
*A61B 17/06* (2006.01)
*A61B 19/02* (2006.01)

(52) U.S. Cl. ..... 206/352; 206/363; 206/380
(58) Field of Classification Search ..... 206/63.3, 206/352, 354, 355, 363–366, 370, 375, 380, 206/570–572, 564; 53/473
See application file for complete search history.

(56) References Cited

U.S. PATENT DOCUMENTS

| | | | | |
|---|---|---|---|---|
| 2,084,540 | A | | 6/1937 | Smith |
| 2,522,213 | A | * | 9/1950 | Doniger ..... 206/375 |
| 2,720,969 | A | | 10/1955 | Kendall |
| 3,013,656 | A | | 12/1961 | Murphy, Jr. |
| 3,696,920 | A | | 10/1972 | Lahay |
| 3,738,251 | A | | 6/1973 | Haaser |
| 4,917,243 | A | | 4/1990 | Abrams et al. |
| 4,935,208 | A | | 6/1990 | Kohler et al. |
| 4,967,914 | A | | 11/1990 | Keeton |
| 4,969,554 | A | | 11/1990 | Sawaya |
| 4,974,728 | A | | 12/1990 | Colton |
| 5,046,612 | A | | 9/1991 | Mostarda et al. |
| 5,085,879 | A | | 2/1992 | Elbaz |
| 5,097,963 | A | | 3/1992 | Chernosky et al. |
| 5,129,615 | A | | 7/1992 | Strauss |
| 5,129,886 | A | | 7/1992 | Sincock |
| 5,339,955 | A | | 8/1994 | Horan et al. |
| 5,348,152 | A | | 9/1994 | Kiyoshi et al. |
| 5,363,862 | A | | 11/1994 | Mercier |
| 5,368,580 | A | | 11/1994 | Suzuki |
| 5,485,917 | A | | 1/1996 | Early |

FOREIGN PATENT DOCUMENTS

| | | |
|---|---|---|
| AU | 500380 | 5/1979 |
| CH | 426095 | 11/1964 |
| FR | 264770 | 11/1990 |
| WO | WO 88/08313 | 11/1988 |
| WO | WO 94/008642 | 4/1994 |

OTHER PUBLICATIONS

Allen & Hamburys Catalogue 1957 Edition (Allen & Hamburys, London), p. 588 Reference No. 49100.

* cited by examiner

*Primary Examiner*—Mickey Yu
*Assistant Examiner*—Jerrold Johnson
(74) *Attorney, Agent, or Firm*—Barnes & Thornburg LLP

(57) ABSTRACT

A container (11) is disclosed for holding a sharp instrument during surgical procedures, the sharp instrument having a handle portion and a cutting portion, the container having an instrument recess (15) adapted to receive at least the cutting portion of the sharp instrument, and guide means (20, 21) for guiding a sharp instrument placed in the container to the instrument recess; the arrangement being such that a sharp instrument received within the instrument recess is positioned therein such that the cutting portion thereof is not directed towards the opening of the instrument recess whereby a user's fingers are substantially prevented from contacting the cutting portion.

12 Claims, 9 Drawing Sheets

CONTAINER FOR SHARP INSTRUMENTS

Matter enclosed in heavy brackets [ ] appears in the original patent but forms no part of this reissue specification; matter printed in italics indicates the additions made by reissue.

CROSS-REFERENCES TO RELATED APPLICATIONS

This application is a U.S. national application (a 371) of international application Ser. No. PCT/AU97/00259 filed Apr. 29, 1997, which claims priority to Australian (AU) Ser. No. PN 9597 filed Apr. 30, 1996.

TECHNICAL FIELD

This invention relates to containers.

The invention has particular but not exclusive application to containers such as trays for use in surgical procedures for holding a sharp instrument having a cutting portion.

As used herein the expression "sharp instrument" includes equipment which can cut, puncture or otherwise be invasive such as scalpels, needles and other sharp or pointed surgical instruments. The expression "cutting portion" is to be taken to include any surface, edge or point which cuts, punctures or is otherwise invasive and includes a scalpel blade and a needle point.

BACKGROUND OF INVENTION

During an operation, a scalpel is transferred between surgeon and scrub nurse or other assistant either directly from hand to hand, or more frequently by one person placing it in a tray for the other to pick up. The tray currently used for this purpose is an open topped kidney shaped dish which provides users with no protection against accidental injury from the scalpel blade. Many other instruments such as suture needles and Veress needles are passed directly between the surgeon and scrub nurse or other assistant.

The present invention aims to provide an alternative to known containers, systems and methods for the handling of sharp instruments during surgical procedures.

SUMMARY OF INVENTION

This invention is one aspect resides broadly in a container for holding a sharp instrument having a handle portion and a cutting portion, the sharp instrument being held within the container to be easily accessible during surgical procedures, the container including:

an instrument recess adapted to receive at least the cutting portion of the sharp instrument, and inclined guide means for guiding a sharp instrument placed in the container to the instrument recess;

the arrangement being such that a sharp instrument received within the instrument recess is positioned therein to be easily accessible for re-use during surgical procedures and such that the cutting portion thereof is not directed towards the opening of the instrument recess whereby a user's fingers are substantially prevented from contacting the cutting portion.

The guide means may converge toward the instrument recess and in a preferred embodiment the container includes inclined walls converging to the opening, the inclined walls constituting the guide means.

In one embodiment the instrument recess is elongated and closed at each end, is adapted to receive a scalpel and along two opposite lengths thereof has a cross sectional configuration of width slightly greater than the major cross-sectional dimension of a scalpel and depth slightly greater than the minor cross-sectional dimension of a scalpel, the length of the instrument recess being such that the scalpel blade is located within one of the opposite lengths irrespective of the position of the scalpel in the instrument recess.

It is preferred that the instrument recess has sidewalls and a base, the junctions thereof being radiussed such that a scalpel is disposed to rest in the recess with its major cross-sectional dimension parallel to the base.

The container may include access means for providing a user with access to the scalpel handle for removing the scalpel from the instrument recess.

The access means could be a pivoting lever arrangement adapted to elevate the scalpel handle portion or alternatively a portion of the container sidewall can pivot to achieve this effect. However the access means is preferably a finger access recess, the cross sectional configuration of the finger access recess being such as to allow a user's fingers to contact the scalpel handle for removing the scalpel from the instrument recess, the position of the finger access recess being such that the scalpel blade is not located within the finger access recess irrespective to eh position of the scalpel in the instrument recess.

The container may include barrier means for preventing a user's fingers entering the instrument recess. The barrier means may constitute the opening to the instrument recess, the width of the opening being such as to allow a scalpel to enter the recess but to prevent a user's fingers entering the recess.

In one preferred embodiment the container may include handle means whereby a user can hold the container. Alternatively, the container may include handle mounting means for mounting a detachable handle whereby a user can hold the container.

In another embodiment the container has a plurality of the instrument recesses each adapted to receive a scalpel therein.

In a further embodiment the container is adapted to contain a suture needle holder and a suturing needle held thereby, and the instrument recess is substantially semi-cylindrical and adapted to receive the suturing needle.

In an alternative embodiment the container is adapted to contain a straight needle and a suture threaded thereto, and the instrument recess is elongated and closed at one end and adapted to receive the straight needle, the container also including a suture recess for receiving the suture. This arrangement may also be included in the container adapted to contain a suture needle holder and a suturing needle.

In another aspect this invention resides broadly in a container for holding a scalpel during surgical procedures, the container including:

an elongated scalpel recess closed at each end and adapted to receive a scalpel, and having two opposite lengths of cross-sectional configuration with width slightly greater than that of the major cross-sectional dimension of the scalpel and depth slightly greater than that of the minor cross-sectional dimension of the scalpel, the length of the scalpel recess being such that the scalpel blade is located within one of the opposite lengths irrespective of the position of the scalpel in the scalpel recess, and guide means for guiding a scalpel placed in the container to the scalpel recess;

the arrangement being such that a scalpel received within the scalpel recess is positioned therein such that the scalpel blade is not directed towards the opening of the scalpel recess whereby a user's fingers are substantially prevented from contacting the scalpel blade.

In a further aspect this invention resides broadly in a container for holding a suture needle holder and a suturing needle held thereby during surgical procedures, the container including:

a substantially semi-cylindrical needle recess adapted to receive the suturing needle therein, and guide means for guiding a suturing needle held by a suture needle holder to the needle recess;

the arrangement being such that a suturing needle received within the needle recess is positioned therein such that the point of the suturing needle is positioned within the needle recess such that a user's fingers are substantially prevented from contacting the point.

In another aspect the invention also resides broadly in a container container for holding a straight needle and a suture threaded thereto, the straight needle and threaded suture being held within the container to be easily accessible during surgical procedures, the container including:

an elongated needle recess closed at one end and adapted to receive a straight needle therein;

a suture recess for receiving the suture, and inclined guide means for guiding a straight needle placed in the container to the needle recess;

the arrangement being such that a straight needle received within the needle recess is positioned therein to be easily accessible for re-use during surgical procedures and such that the point of the straight needle is positioned within the needle recess such that a user's fingers are substantially prevented from contacting the point.

In another aspect this invention resides broadly in a method of transferring a sharp instrument having a handle portion and a cutting portion between operators during a surgical procedure, wherein:

the transferor of the sharp instrument places the sharp instrument in an instrument recess in an instrument holding container, the sharp instrument being held within the container to be easily accessible during surgical procedures, and the received or transferee of the sharp instrument removes the sharp instrument from the instrument recess;

the instrument recess being adapted to receive at least the cutting portion of the sharp instrument, and the instrument holding container having inclined guide means for guiding a sharp instrument placed therein to the instrument recess, the arrangement being such that a sharp instrument received within the instrument recess is positioned therein to be easily accessible for re-use during surgical procedures and such that the cutting portion thereof is not directed towards the opening of the instrument recess whereby an operator's fingers are substantially prevented from contacting the cutting portion.

DESCRIPTION OF DRAWINGS

In order that this invention may be more easily understood and put into practical effect, reference will now be made to the accompanying drawings which illustrate a preferred embodiment of the invention, wherein.

DESCRIPTION OF PREFERRED EMBODIMENT OF INVENTION

Figure 1:
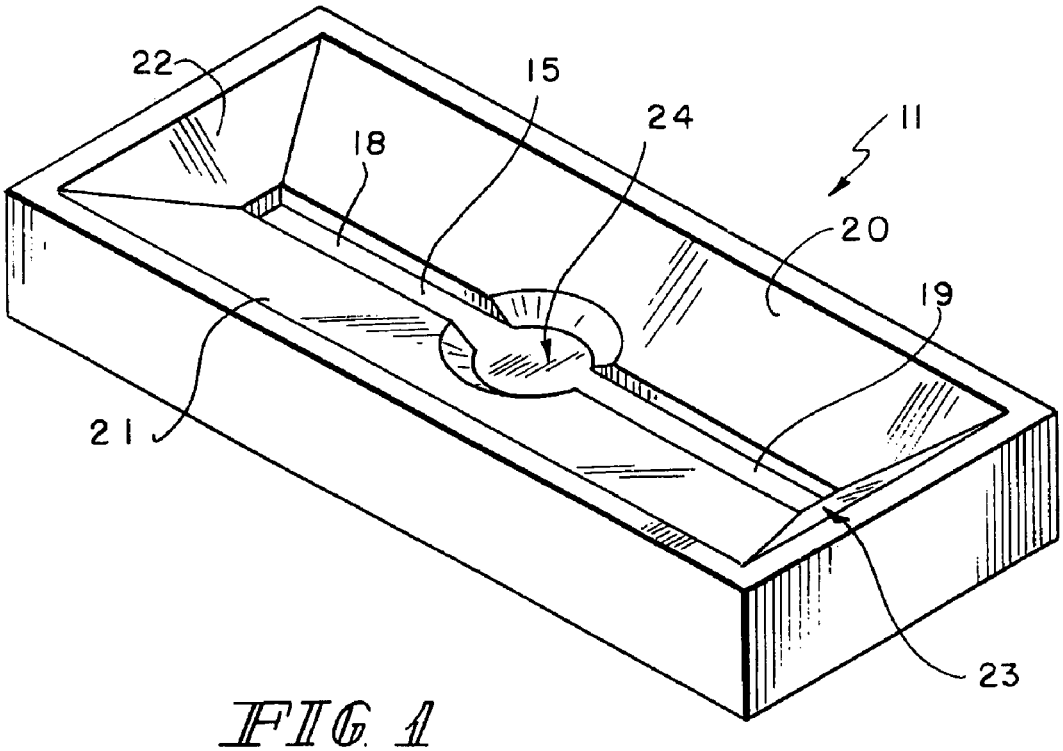
FIGS. 1 and 1A respectively are perspective and plan views of a container in accordance with the invention for holding a scalpel.
Figure 1A:
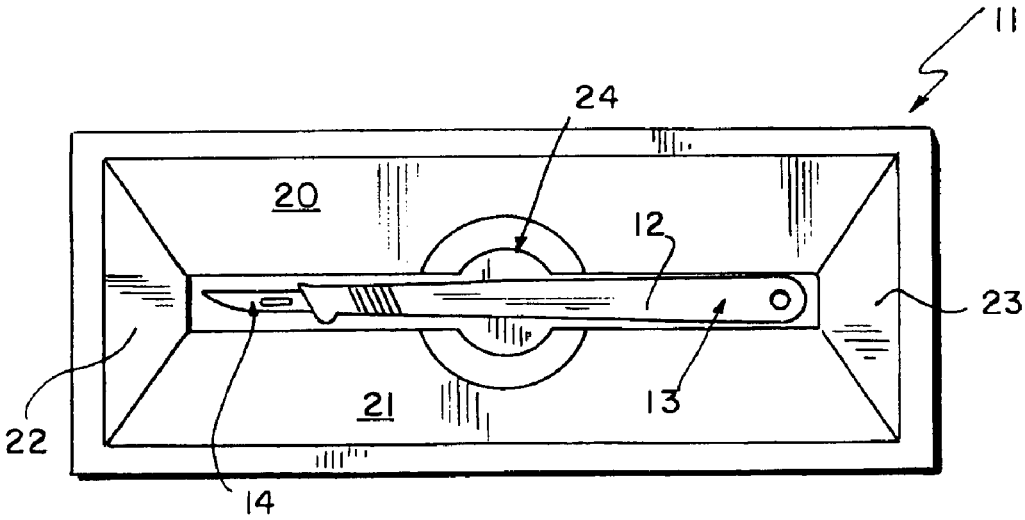

FIGS. 1 and 1A illustrate a first embodiment of a container 11 for safely container a scalpel 12 having a handle 13 and blade 14. Container 11 has an elongated recess 15 which is closed at each end 16,17 and receives scalpel 12 as seen in FIG. 1A. Scalpel recess 15 has two opposite portions 18 and 19. The width of scalpel recess 15 is slightly greater than that of the major cross-sectional dimension of scalpel 12 (the dimension along the cutting axis, usually the depth of handle 13) and the depth of scalpel recess 15 is slightly greater than that of the minor cross-sectional dimension of the scalpel (usually the width of handle 13).

Sloping side walls 20,21 constitute guide means which guide scalpel 12 when placed in placed in container 11 toward scalpel recess 15. Sloped end walls 22,23 also guide the scalpel to toward the scalpel recess.

Intermediate opposite portions 18,19 of scalpel recess 15, finger access recess 24 provides a user with access to scalpel handle 13 for removing scalpel 12 from scalpel recess 15. Finger access recess 24 has a cross sectional configuration such as to allow a user's fingers to contact the scalpel handle for removing the scalpel from the scalpel recess. Finger access recess 24 is positioned along scalpel recess 15 such that scalpel blade 14 is not located within finger access recess 24 irrespective of the position of scalpel 12 in scalpel recess 15. Moreover the length of scalpel recess 15 is such that scalpel blade 14 is located within one of portions 18,19 irrespective of the position of scalpel 12 in scalpel recess 15 and irrespective of the type of scalpel being used.

Thus the shortest of the available blade and handle combinations, which will of course have the largest fore and aft movement in the recess, will still have its sharp blade positioned outside the central finger access recess.

By suitably configuring the length of scalpel recess 15 and the length of finger access recess 24, container 11 is designed to have a universally accommodating all scalpels in a manner such that a scalpel received within the scalpel recess is positioned therein such that the cutting edge of scalpel blade 14 is located in finger access recess 24, and is not directed towards the opening or upper entrance of scalpel recess 15. Accordingly a user's fingers are substantially prevented from contacting scalpel blade 14.

The downwardly sloping side and end walls mean that the less precision is required by users when replacing the scalpel in the container. The downwardly sloping side walls, and also the end walls, direct the scalpel positively toward the scalpel recess. Both scalpel blades and scalpel handles are wider than they are thick, and the scalpel is thus disposed to come to rest in a flat position in the base of the scalpel recess. In this position the sharp scalpel blade is below the upper edge of the scalpel recess. The low centre of gravity of the container and its relatively wide base provide stability on uneven surfaces such as when placed on a patient's person during a surgical procedure or operation.

Figures 5A, 5B, 5C, 5D, 5E:
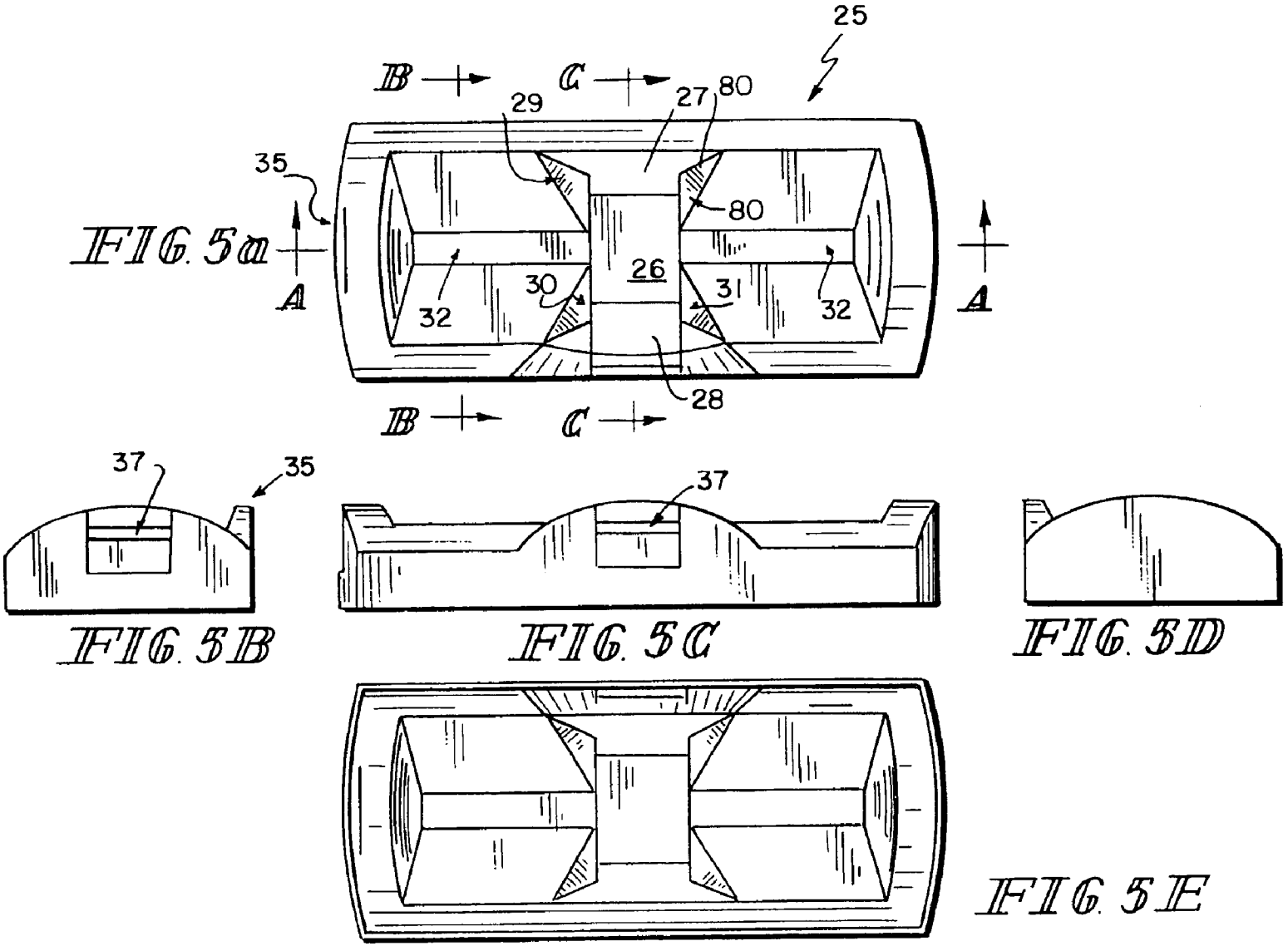
FIGS. 5A to 5E illustrate another embodiment of a container for a scalpel which has a mounting for a handle the illustrations being plan, end, side, end and base elevations respectively.
Figure 6A:
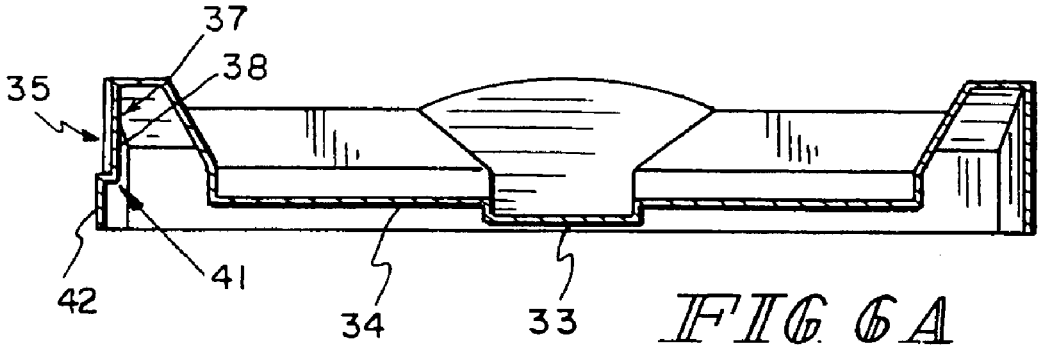
FIGS. 6A to 6C are cross-sectional elevations at sections AA, BB and CC as indicated in FIG. 5A.
Figure 6C:
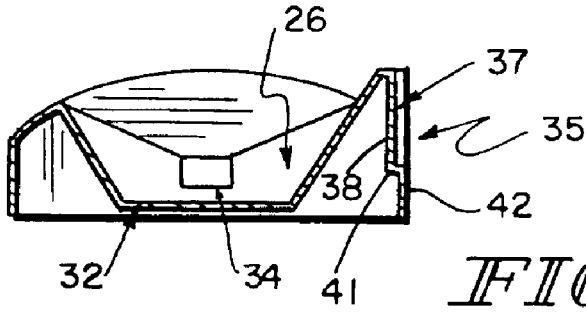
Figure 6B:
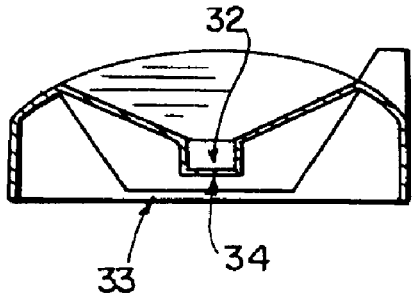

FIGS. 5A to 5E are plan, end, side, end and base elevations respectively of an alternative container 25 for a scalpel. FIGS. 6A to 6C are cross-sectional elevations at sections AA, BB and CC are indicated in FIG. 5A. It can be seen that the finger access recess 26 of container 25 has sloping side walls 27,28 and opposed sloping end walls 29,30 and 80,31 on either side of scalpel recess 32. The base 33 of finger access recess 26 extends below the base 34 of scalpel recess 32 to better facilitate the removal from container 25 of a scalpel resting to scalpel recess 32.

Figure 7A:
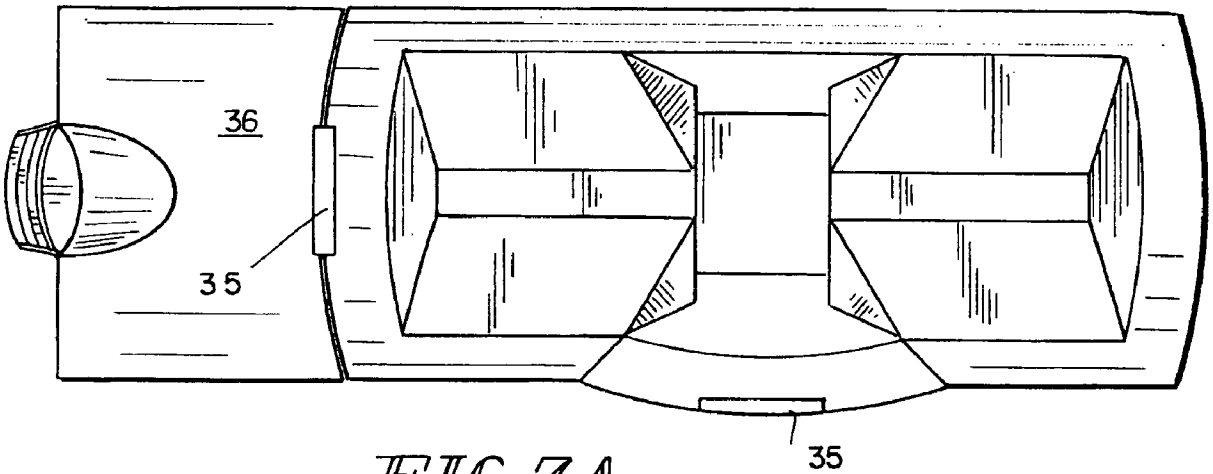
FIGS. 7A and 7B correspond to FIGS. 5A and 6A respectively and illustrate a handle mounted in the end mounting bracket mounting.
Figure 7B:
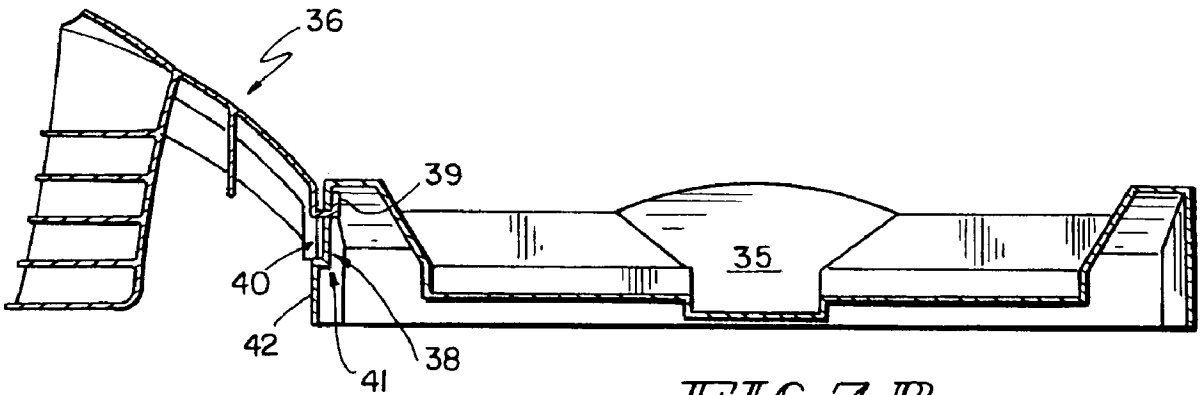

One end and one side of container 25 each have a mounting assembly 35 for receiving therein and mounting a handle 36 (as seen in FIGS. 7A and 7B). Mounting assembly 35 has a cut out slot 37 in a recessed end or side wall 38 which can receive the locking lip 39 of handle 36 as best seen in FIG. 7B. A stub portion 40 of handle 36 then sits in heel 41 where recessed end or side wall portion 38 steps out to meet main end or side wall portion 42.

Figure 8A:
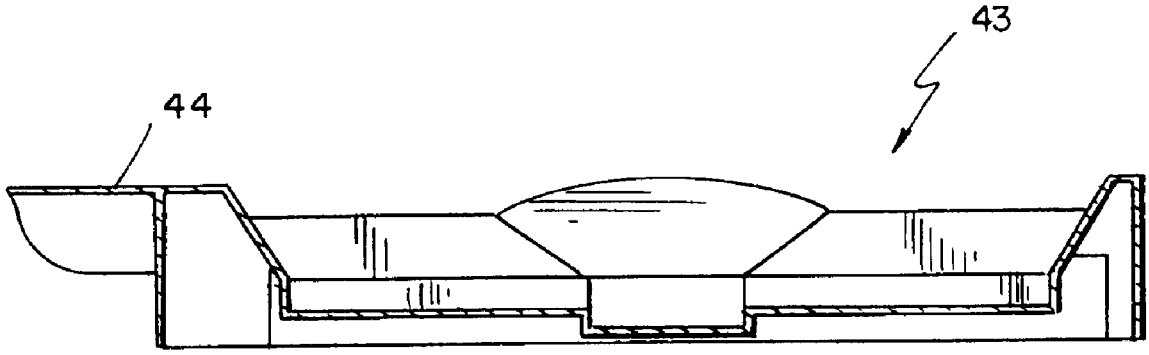
FIGS. 8A to 8C are sectional elevations illustrating another embodiment of the scalpel tray with integral handles formed at an end and side, the sectional elevations corresponding with the sections AA, BB and CC indicated in FIG. 5A, and FIGS. 9 and 10 illustrate cross-sectional elevations of alternatively shaped recesses for receiving a scalpel.
Figure 8B:
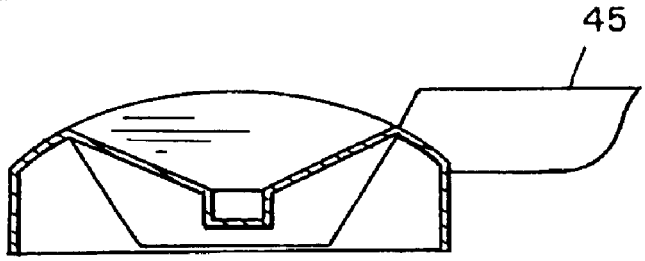
Figure 8C:
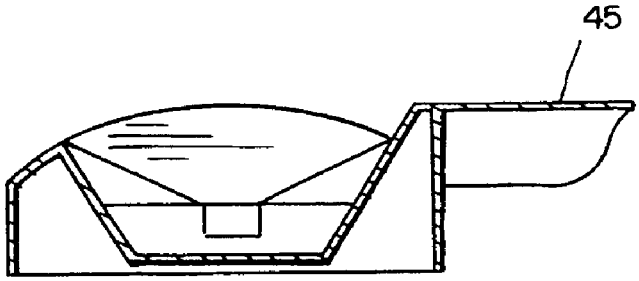

Alternatively, as seen in FIGS. 8A to 8C, container 43 may be integrally provided with end and side handles 44 and 45.

Figure 9:
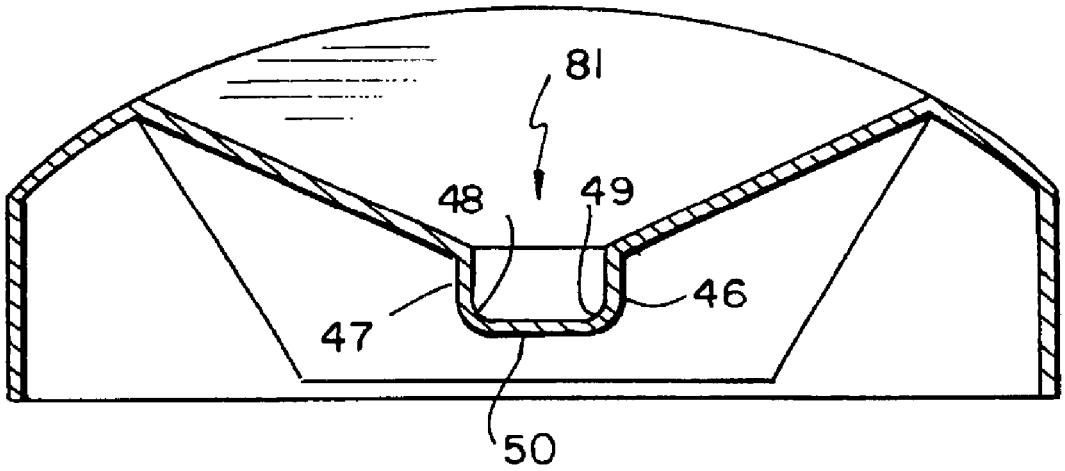

As can be seen in FIG. 9, the sidewalls 46,47 of the scalpel recess 81 can be radiussed at 48,49 to the base 50 of the recess such that a scalpel is disposed to rest in the recess with its major cross-sectional dimension parallel to the base. This even further reduces the already statistically remote possibility that a scalpel will fall into the recess and come to rest with the back of the handle in the junction between the recess sidewall and base and consequently with the scalpel blade uppermost.

Figure 10:
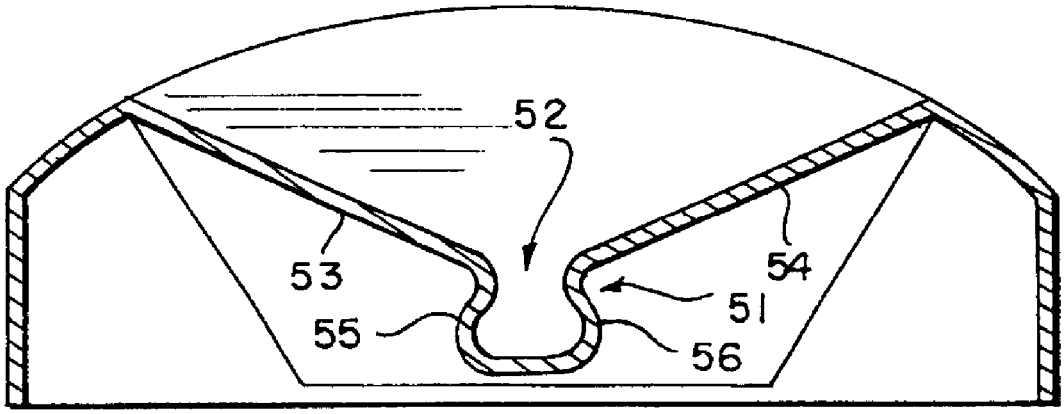

In another embodiment seen in FIG. 10, the container can be provided with a barrier for preventing a user's fingers entering the instrument recess. The barrier is formed by narrowing the opening or entrance neck 51 of scalpel recess 52 so that the width of the opening is such as to allow a scalpel to enter the recess as it slides along the flat of the scalpel handle down the sloping sidewalls 53,54 towards neck 51, but to prevent a user's fingers entering the recess.

The upper edges of the recess sidewalls 55,56 are greatly sloped and radiussed towards neck 51 so that when a scalpel is being removed from the tray under the action of a user's fingers, the flat of the handle will slide upwardly over one of recess sidewalls 55,56 so that it presents to neck 51 with its narrow handle width transverse to the opening.

Figure 2:
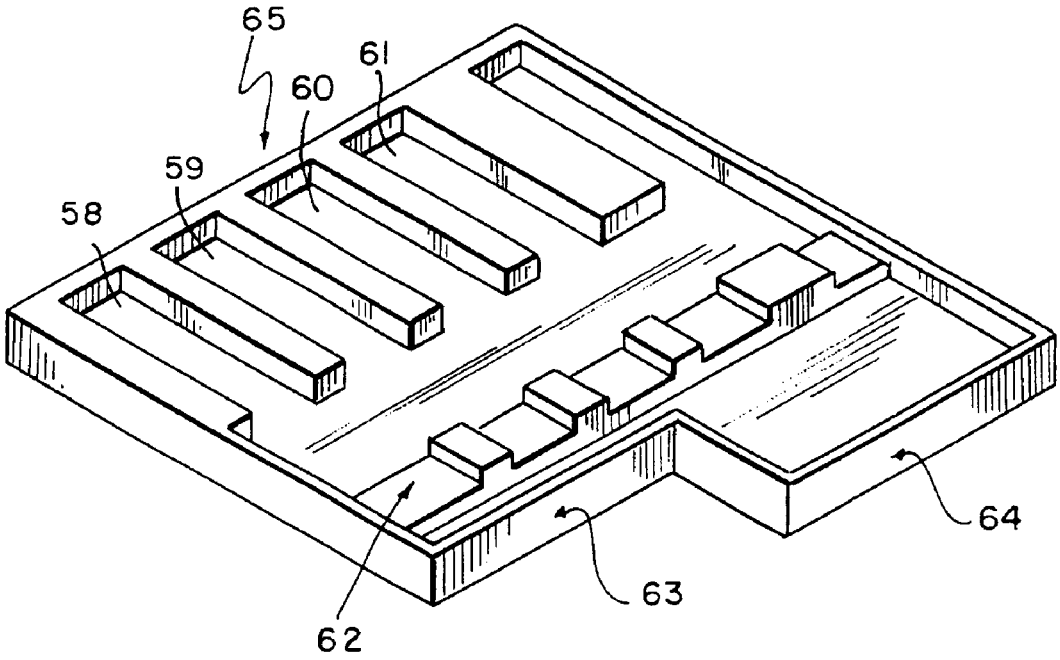
FIGS. 2 and 2A respectively are perspective and plan views of a container in accordance with the invention for holding a plurality of scalpels.
Figure 2A:
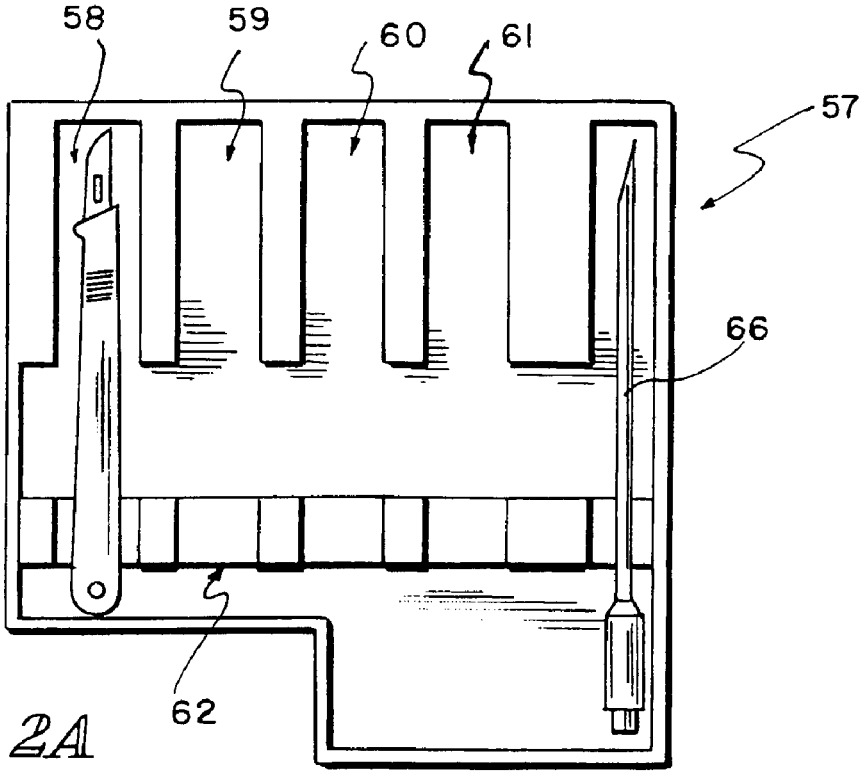

FIGS. 2 and 2A respectively illustrate a container 57 for holding more than one scalpel and has a plurality of the recess 58-61 each adapted to receive a scalpel. The multiple scalpel container has a raised section 62 located beneath that portion of the container which will contain the scalpel handles. This allows the user to safely grasp the handle and remove or replace the scalpel blade and its handle into the tray. The recessed area for the scalpel blade minimises the chance of the user accidentally injuring themselves on the sharp scalpel blade. The raised edge wall 63,64 located behind the blade handles combines with the endwall 65 to limit fore and aft movement of a scalpel in a manner described above to minimise the potential of the blade coming into contact with the user's fingers. This provides safely for the user when grasping the handle to remove the scalpels from the tray. Raised section 62 beneath the scalpel handle elevates the handle above the main baseplate section and provides sufficient room for a user to grasp the handle when removing the scalpel.

The tray illustrated stores up to four blades and their handles, two long and two short handles fitted with a variety of scalpel blades. This unit also features a recessed area for the safe storage of long Veress needles 66 used for the introduction of gas into the abdominal cavity for visualisation of the abdominal and pelvic cavities during surgical operations. The tray will prove useful where more than one scalpel blade is used during a surgical operation as it provides a safe means of storing scalpel blades when they are not in use. The majority of surgical operations require the use of more than one scalpel blade. The tray has a low centre of gravity and being of substantially square shape is stable when positioned on an instrument trolley, thereby reducing the risk of its contents falling out and causing injury.

Figure 3:
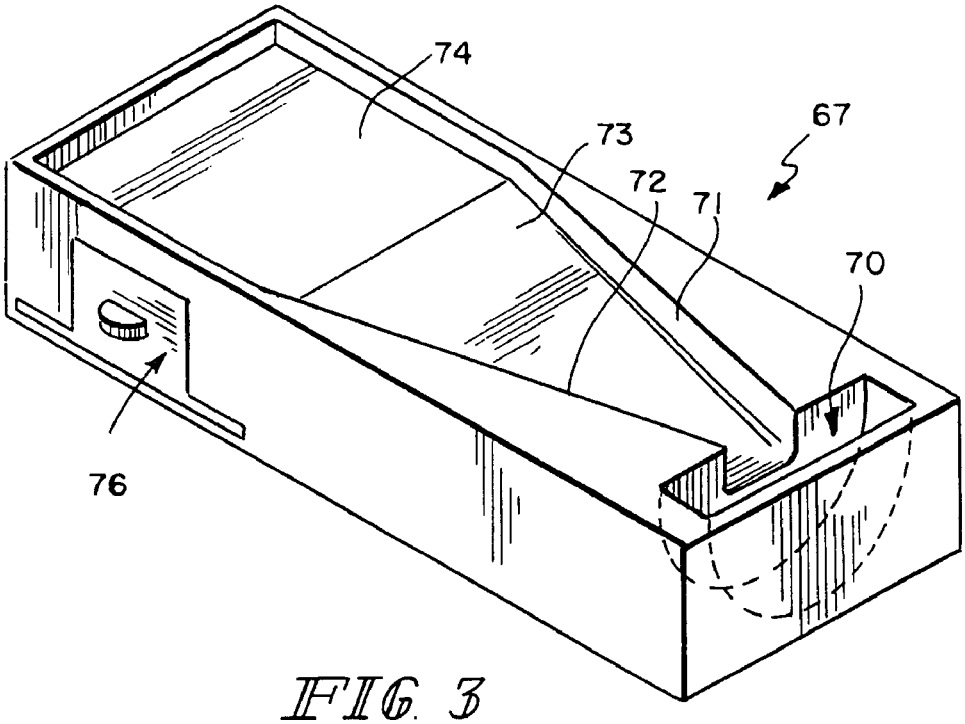
FIGS. 3 and 3A respectively are perspective and plan views of a container in accordance with the invention for holding a suturing needle holder and a suture needle held thereby.
Figure 3A:
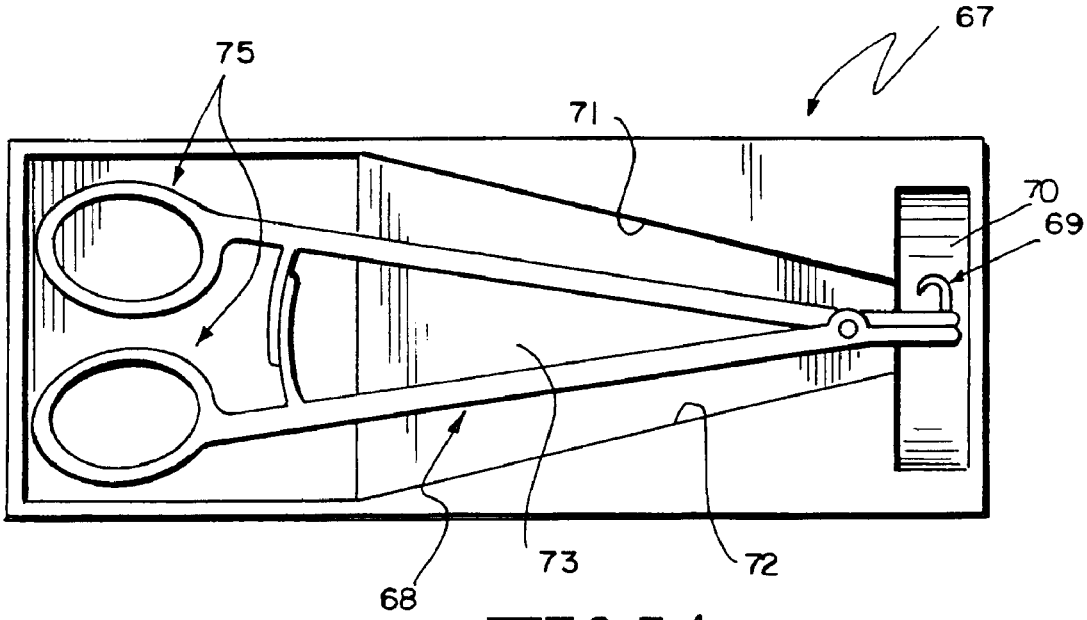

FIGS. 3 and 3A illustrate a container 67 for holding a suturing needle holder 68 and a suture needle 69. Container 67 has a substantially semi-cylindrical recess 70 adapted to receive suturing needle 69. Container 67 has a pair of downwardly converging side walls 71, 72 on either side of ramp 73 which constitute guide means for guiding suturing needle 69 held by holder 68 to needle recess 70. The arrangement is such that the substantially semi-circular suturing needles 69 are received within needle recess 70 and positioned therein such that the point of the suturing needle is positioned within recess 70 such that a user's fingers are substantially prevented from contacting the point. Recess 70 also houses the suture material. An elevated flat surface 74 is located at the end of the container remote from recess 70.

A needle holder is shaped like a pair of long fine pliers with a handle locking mechanism. When a holder 68 fully loaded with needle 69 and a suture (not illustrated) is placed into container 67, the suture needle 69 sits below the middle sloping section 73 in a recess 70 and the width of recess 70 allows little fore and aft movement thus offering stability for the needle holder and its attached suture needle. Moreover the point of the suture needle is below the middle ramp section 73 thereby minimising the risk of a user's fingers accidentally coming into contact with the sharp needle. Because the middle ramp section 73 slopes downwards towards the recess 70, the finger grips 75 of needle holder 68 are elevated above flat surface 74 thereby allowing user's fingers sufficient room to be inserted and facilitating removal of needle holder 68 from the container. The unit could be manufactured to suit a variety of needle holder sizes. The low rectangular design of the container provides stability when placed on a patient's person during an operation.

Figure 4:
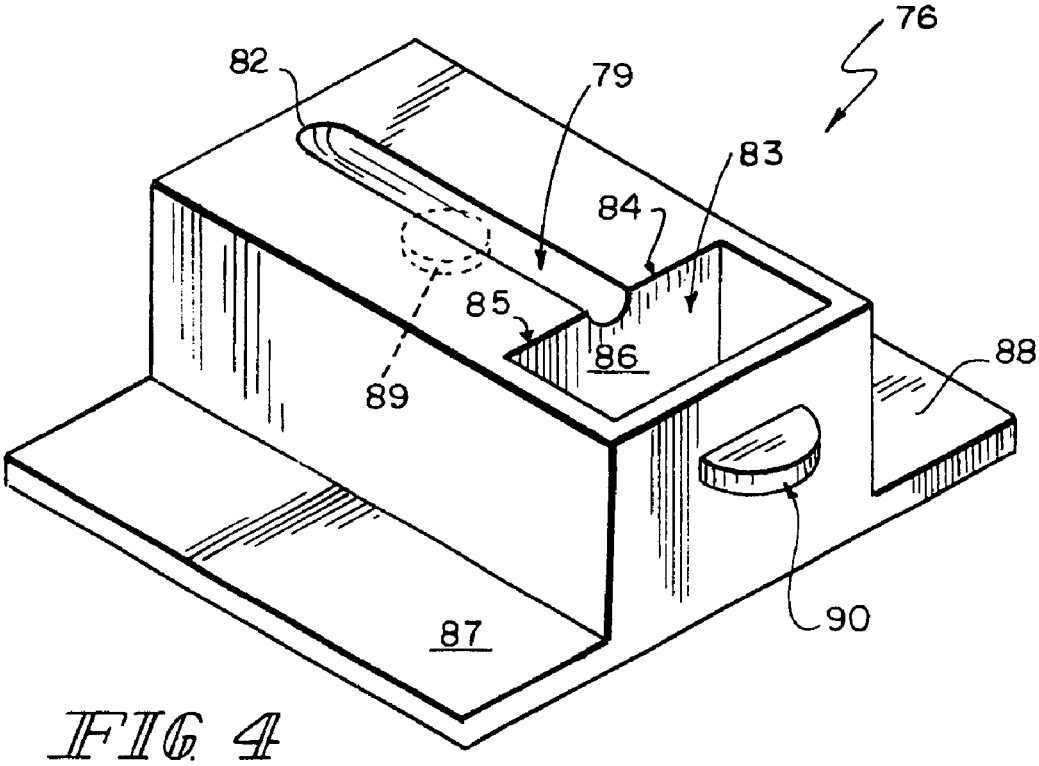
FIGS. 4 and 4A respectively are perspective and plan views of a container in accordance with the invention for holding a straight needle and threaded suture.
Figure 4A:
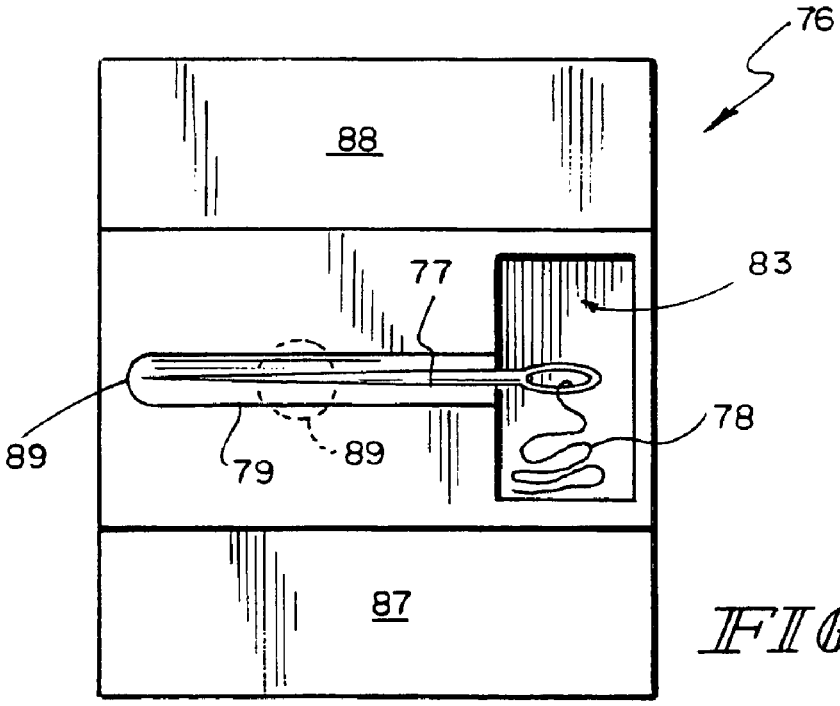

FIGS. 4 and 4A illustrate a container 76 which can be incorporated into container 67 (as seen in FIG. 3) and which is adapted to contain a straight needle 77 and a suture 78 threaded thereto. Needle recess 79 is elongated and closed at one end 82. Container 76 also has a suture recess 83 for receiving suture 78 threaded to needle 77. Needle recess 79 opens into suture recess 83 and edges 84,85 of suture recess wall 86 constitute guide means for guiding a user placing a straight needle in container 76 within needle recess 79. The arrangement is such that a straight needle received within the needle recess is positioned therein such that the point of the straight needle is positioned within the needle recess such that a user's fingers are substantially prevented from contacting the needle point. The base of container 76 extends outwardly to provide wings 87,88 on either side of the container. As seen in FIG. 3, these wings facilitate a sliding drawer function when container 76 is incorporated in container 67. Handle 90 allows container 76 to be easily removed from the underside of the suture needle tray 67. The relatively wide baseplate formed by wings 87,89 also provides stability enabling the container to be placed on a patient's person during an operation.

Suture recess serves the dual purpose of maintaining suture 78 in a sterile environment and provides sufficient room for a user's fingers to grasp the blunt end of the needle. Straight suture needles are very fine and are therefore very light in weight. To ensure that the light needle does not become dislodged during transfer, a small magnet 89 is positioned beneath needle recess 79.

The containers described above can be made from a range of suitable material as will be well known to those skilled in the art. If intended to be re-used they can be made from autoclavable plastic and will include sufficient steam ventilation holes for autoclaving purposes. Alternatively if intended to be disposable, they can be made cheaply from a suitable plastics material.

In use during surgical procedures, it will be appreciated that containers in accordance with the present invention utilise a principle conferring significant advantages over existing methods, systems and equipment. Sharp instruments are traditionally passed between surgeons, scrub nurses and other theatre staff either directly hand to hand, or by being placed in a container such as a conventional general purpose kidney bowl.

However in accordance with the present invention, the dangers of needle stick injury or other injury from a non-sterile sharp instrument which may have been invasively used on a patient are significantly reduced by utilising a specific purpose-designed container in which the sharp instrument is positioned by the transferor of the sharp instrument and from which the sharp instrument is removed by the transferee or receiver of the sharp instrument, the container of the present invention being such that the sharp instrument is received within an instrument recess and positioned therein such that the cutting portion of the instrument is not directed towards the opening of the instrument recess whereby the fingers of the transferor or transferee are substantially prevented from contacting the cutting portion.

The scalpel container provides substantially advantages and is an improvement on the traditional kidney tray which being an open topped disk gives little if any protection to users against accidental injury from the scalpel blade. Injury from scalpel blades carry the possibility of an operator contacting a serious or fatal disease and the present invention significantly minimises this risk.

The present invention also improves upon the current method for storing scalpels on a scrub nurse's instrument trolley (which is simply to place them into an open kidney shaped disk or to leave them sitting loosely on the sterile cloth drape which covers the instrument trolley). Removing the blade and its handle from these kidney dishes involves the risks mentioned above, and storing them loosely on the drapes not only involves the same risk but also carries the risk of the sharp blade penetrating the cotton trolley drape and rendering the blade tip unsterile. This would then render the cloth trolley unsterile as well and would also put the patient at risk of contracting an infection.

The suturing needle container also has a number of significant advantages. Suture materials vary in length and in elasticity and some modern materials are very loose and fall freely under gravity to their full length. In an operating theatre anything that falls below scrub nurse waist level is deemed to be unsterile and endangers the patient of contracting an intra-operative infection. This frequently occurs with known methods of needle holder and suture transfer between surgeon and scrub nurse. Storing all the suture material in the dished recessed area of the tray avoids this problem. The tray also protects the patient against needle stick injury. Often when the scrub nurse is busy, the surgeon if finished the operation will place a needle holder with a suture needle loaded onto it onto the drapes covering the patient. This can then penetrate the drapes and injure the patient. Personal transfer of a loaded needle holder from one person to another, as commonly occurs in known systems, carries a high risk of needle stick injury. The suture tray of the present invention significantly minimizes all these risks.

The physical transfer of straight needles between members of a surgical team also involves an extremely high risk of needle stick injury and this is also significantly minimised by the straight needle container of the present invention.

It will of course be realised that whilst the above has been given by way of an illustrative example of this invention, all such and other modifications and variations hereto, as would be apparent to persons skilled in the art, are deemed to fall within the broad scope and ambit of this invention as is herein set forth.

What is claimed is:

1. An apparatus comprising a scalpel and a container holding said scalpel, said scalpel including:

a blade attached to a handle, said scalpel having a major cross-sectional dimension and a minor cross-sectional dimension; and said container including:

an elongated scalpel recess closed at each end and receiving said scalpel, and having a first portion receiving said scalpel blade and a second portion receiving at least part of said scalpel handle, said portions having a width slightly greater than that of the major cross-sectional dimension of the scalpel and depth slightly greater than that of the minor cross-sectional dimension of the scalpel, the length of said scalpel recess being such that the scalpel blade is located within one of said portions irrespective of the position of the scalpel in the scalpel recess, *the width being substantially constant for the length of each of said portions,* and guide means for *physically* guiding a scalpel placed in said container [to] *at a position outside of said recess into* said scalpel recess;

the [arrangement] *scalpel recess* being [such that] *constructed so* the scalpel received within said scalpel recess is positioned therein such that the scalpel blade is not directed towards the opening of the scalpel recess whereby a user's fingers are substantially prevented from contacting a cutting portion of the scalpel blade.

2. An apparatus as claimed in claim 1, wherein said container includes inclined walls converging to said opening, the inclined walls constituting said guide means.

3. An apparatus as claimed in claim 1, wherein said scalpel recess has sidewalls and a base, the junctions thereof being radiussed such that a scalpel is disposed to rest in the recess with its major cross-sectional dimension parallel to said base.

4. An apparatus as claimed in claim 1, said container including access means for providing a user with access to the scalpel handle for removing the scalpel from said scalpel recess.

5. An apparatus as claimed in claim 4, wherein said access means includes a finger access recess, the cross sectional configuration of said finger access recess being such as to allow a user's fingers to contact the scalpel handle for removing the scalpel from said scalpel recess, the position of said finger access recess being such that the scalpel blade is not located within said finger access recess irrespective of the position of the scalpel in the instrument recess.

6. An apparatus as claimed in claim 1, said container including barrier means for preventing a user's fingers from entering said scalpel recess.

7. An apparatus as claimed in claim 6, wherein said barrier means constitutes the opening to said scalpel recess, the width of said opening being such as to allow a scalpel to enter the recess but to prevent a user's fingers entering the recess.

8. An apparatus as claimed in claim 1, said container including handle means whereby a user can hold the container.

9. An apparatus as claimed in claim 1, said container including handle mounting means for mounting a detachable handle whereby a user can hold the container.

10. An apparatus as claimed in claim 1, said container including a plurality of said scalpel recesses each adapted to receive a scalpel therein.

11. [A container for holding a suture needle holder and a suturing needle held thereby during surgical procedures] *An apparatus comprising a suture needle holder, a suturing needle being held thereby, and a container holding said suture needle holder*, the container including:

a substantially semi-cylindrical needle recess adapted to receive the suturing needle therein, and guide means for *physically* guiding a suturing need held by a suture needle holder [to] *at a position outside said recess into* said needle recess;

[the arrangement being such that] *wherein* a suturing needle received within said needle recess is positioned therein such that the point of the suturing needle is positioned within the needle recess such that a user's fingers are substantially prevented from contacting the point.

12. A method of retrievably and temporarily storing a scalpel between uses of the scalpel during a surgical procedure, said scalpel having a handle portion and a blade and having a major cross-sectional dimension and a minor cross-sectional dimension, said method comprising:

placing the scalpel held by an operator into an instrument recess in an instrument holding container, the scalpel being held within the container to be easily accessible during surgical procedures, and removing the scalpel by the operator from the instrument recess, said instrument recess *having a length longer than the length of the scalpel and said instrument being* closed at each end and adapted to receive said scalpel, and having a first portion adapted to receive said scalpel blade and a second portion adapted to receive at least part of said scalpel handle, said portions having a width slightly greater than that of the major cross-sectional dimension of the scalpel and depth slightly greater than that of the minor cross-sectional dimension of the scalpel, the length of said scalpel recess being such that the scalpel blade is located within one of said portions irrespective of the position of the scalpel in the scalpel recess, and said instrument holding container having inclined guides for guiding a scalpel placed therein to said instrument recess, the arrangement being such that a scalpel received within said instrument recess is [position] *positioned* therein to be easily accessible for re-use during surgical procedures and such that the cutting portion thereof is not directed towards the opening of the instrument recess whereby an operator's fingers are substantially prevented from contacting said cutting portion.

* * * * *